(12) United States Patent
Cook, Jr.

(10) Patent No.: US 6,248,061 B1
(45) Date of Patent: Jun. 19, 2001

(54) SUCTIONING LARYNGOSCOPE BLADE

(76) Inventor: Lewis L. Cook, Jr., P.O. Box 1643, Albany, NY (US) 12201

( * ) Notice: Subject to any disclaimer, the term of this patent is extended or adjusted under 35 U.S.C. 154(b) by 0 days.

(21) Appl. No.: 09/434,194

(22) Filed: Nov. 4, 1999

(51) Int. Cl.$^7$ ................................................. A61B 1/267
(52) U.S. Cl. ........................................ 600/187; 600/205
(58) Field of Search ................................. 600/205, 187

(56) References Cited

U.S. PATENT DOCUMENTS

| | | |
|---|---|---|
| 2,854,004 | 9/1958 | Durrant . |
| 2,911,968 * | 11/1959 | Scheuler et al. ................... 600/187 |
| 4,049,000 * | 9/1977 | Williams .............................. 600/205 |
| 4,947,896 | 8/1990 | Bartlett . |
| 5,287,848 | 2/1994 | Cubb et al. . |
| 5,392,764 * | 2/1995 | Swanson et al. .................... 600/187 |
| 5,431,152 | 7/1995 | Flam et al. . |
| 5,571,071 * | 11/1996 | Shamro .............................. 600/187 |
| 5,702,351 | 12/1997 | Bar-Or et al. . |
| 5,897,489 | 4/1999 | Urbanowicz et al. . |

* cited by examiner

Primary Examiner—Paul J. Hirsch
(74) Attorney, Agent, or Firm—Hoffman, Warnick & D'Alessandro LLC; Ronald A. D'Alessandro

(57) ABSTRACT

A suctioning laryngoscope blade is provided that allows a user to efficiently suction the airway of a patient without increasing costs or time for the user. More particularly, a suctioning laryngoscope blade is provided that includes a blade portion and a suction tube, coupled to an external surface of the blade portion, wherein the suction tube is a permanent component of the laryngoscope blade.

20 Claims, 5 Drawing Sheets

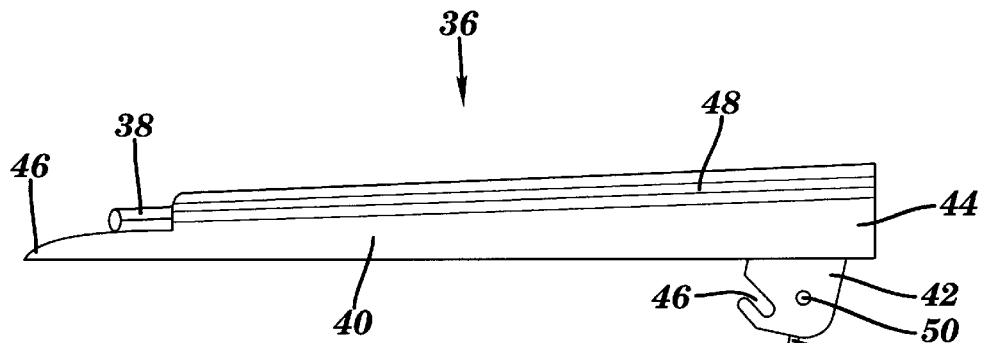
FIG. 3
_RELATED ART_
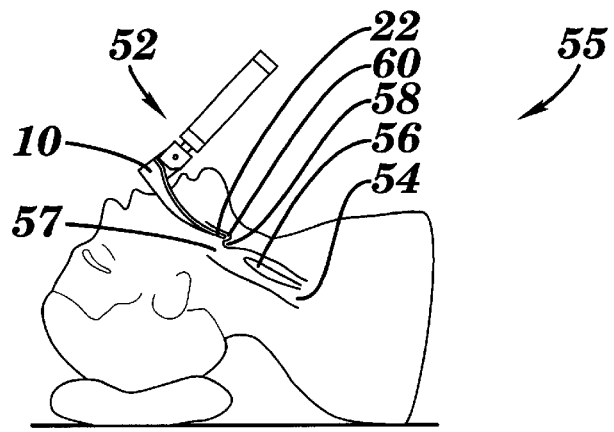
FIG. 4
_RELATED ART_
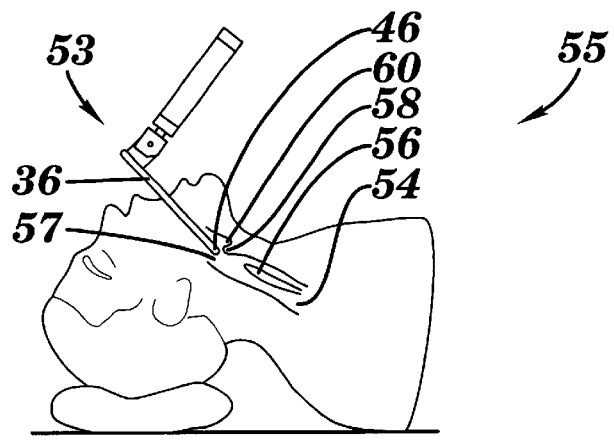
FIG. 5
_RELATED ART_

SUCTIONING LARYNGOSCOPE BLADE

BACKGROUND OF THE INVENTION

1. Technical Field

The present invention generally relates to a suctioning laryngoscope blade, and more particularly to a laryngoscope blade that includes a suction tube permanently affixed thereto for the efficient clearance of the airway of a medical patient during endotracheal intubation.

2. Background Art

During medical emergencies, the need to aid a patient's breathing often becomes necessary. A laryngoscope is a device used by medical professionals during a procedure known as endotracheal intubation. Endotracheal intubation is a procedure by which a patient's airway is manipulated so a medical tube, carrying air or medicines, can be delivered through the airway.

Typical laryngoscopes include a handle that carries batteries or another similar power source. Attached to the handle is a blade portion that may include a light source. The medical professional will position the blade portion of the laryngoscope in the oropharynx of a patient in an attempt to gain access to the patient's airway. During this step the light source on the blade portion will illuminate and give the medical professional an improved view of the patient's airway.

Problems exist, however, during the intubation of a patient when the airway is blocked by vomit, blood or the like, which obstructs the user's view and blocks the insertion of the medical tube. In such cases, suction is necessary to remove the blockages and clear the airway for the insertion of the tube. Previously, medical professional were forced to hold the laryngoscope in one hand and a suction tube in the other, leaving no hand free for insertion of the medical tube. Alternatively, medical professionals have attempted to hold both the laryngoscope and the suction tube with one hand while inserting the medical tube with the other. However, the efficient and accurate manipulation of both the suction tube and the laryngoscope is prevented by utilizing such a technique.

Heretofore, many have attempted to alleviate such problems by incorporating suction tubes into laryngoscope devices. Examples of such devices include the following references, all of which are hereby incorporated by reference.

U.S. Pat. No. 2,854,004 to Durrant teaches a laryngoscope blade that has a suction tube extending along a surface thereof. A problem with the device of Durrant is that the suction tube is not permanently coupled to the blade. In contrast, the suction tube can be attached and detached at the whim of a user. Such a feature leads to increased costs in disposal of the suction tube or in an additional cleaning step for sanitizing the tube separately from the blade. In addition, by using a suction tube that is not permanently affixed to the blade or formed as a component of the blade, there is an increased risk that the suction tube will become separated from the blade during intubation. Such a separation results in the reduced suctioning of the patient's airway and accordingly, continued obstruction thereof. Similarly, U.S. Pat. No. 4,947,896 to Bartlett, U.S. Pat. No. 5,431,152 to Flam et al., and U.S. Pat. No. 5,897,489 to Urbanowicz et al. all teach a laryngoscope that may incorporate an attachable suction tube. In particular, the device of Bartlett utilizes a channel and/or passageway for the insertion of a tubular member for the suctioning of a patient's airway. Moreover, the device of Flam et al. allows for a suction tube to be extend along a surface of the blade, and the device of Urbanowicz et al. utilizes a clip for the temporary attachment of a suction tube to a laryngoscope. All of these devices face the same problems as the device of Durrant.

U.S. Pat. No. 5,287,848 to Cubb et al. provides a passageway through the body of a laryngoscope through which a suction tube is passed. However, similar to the above devices, the use of a suction tube that is separate from the laryngoscope results in additional cost and/or cleaning for the user. Moreover, the device of Cubb et al. is extremely bulky and, accordingly, makes the efficient manipulation of the airway of a patient highly difficult.

U.S. Pat. No. 5,702,351 to Bar-Or et al. provides a disposable laryngoscope blade that is preferably made of plastic. Through the body of the blade, a channel is provided to which suction is directly applied to eliminate the need for a separate tube. However, when providing such a suction means, a user is limited in the volume of obstructions that can be removed. In particular, the device of Bar-Or et al. discloses a narrow channel through the body of the blade. Since the blade portion engages the interior of a patient's throat, it needs to be sleeker and more "blade-like." Accordingly, any channel formed within the blade is likewise required to be of small dimensions. As such, the passageway is more prone to becoming blocked or obstructed than a larger tube-like structure coupled to an exterior surface of the blade. In addition, the device of Bar-Or et al. is disposable and formed from plastic. Such a blade is not only weaker in structure than traditional stainless steel blades but will also require the user to purchase a new blade for every use.

Therefore there exists a need for a laryngoscope blade that includes a suction means that will not increase the costs to a user and will be sufficiently secured to the blade so as to maintain optimal levels of suction. In particular, there exists the need for a laryngoscope blade having a suction tube permanently affixed/coupled thereto such that the suction tube is a permanent component of the laryngoscope blade. This is so that the laryngoscope blade will remain sleek in profile for the efficient manipulation of a patient's airway.

SUMMARY OF THE INVENTION

The present invention overcomes the deficiencies of the related art by including a laryngoscope blade that includes a blade portion and a suction tube permanently affixed thereto such that blood, vomit, or other obstructions can be efficiently removed from the airway of a patient. As used herein, tube means any hollow member, such as a catheter, through which suction can be applied. Moreover, the present invention overcomes the deficiencies of the related art by providing a suction tube that is a permanent component of a laryngoscope blade so that additional sanitization steps and/or costs are eliminated. In addition, the present invention overcomes the problems of the related art by providing a suctioning laryngoscope blade that maintains a sleek, non-bulky structure.

According to a first aspect of the present invention, a laryngoscope blade is provided, which includes: (1) a blade portion; and (2) a suction tube, coupled to an external surface of the blade portion, wherein the suction tube is a permanent component of the laryngoscope blade.

According to a second aspect of the present invention, a laryngoscope blade is provided, which includes: (1) a metal blade portion; and (2) a metal suction tube permanently fixed to an external surface of the blade portion.

According to a third aspect of the present invention, a laryngoscope blade is provided, which includes: (1) a blade portion; (2) a suction tube external to and permanently fixed to the blade portion, wherein the suction tube includes an adaption end and a suction end; and (3) wherein the adaption end is attachable to a suction source.

It is therefore an advantage of the present invention to provide a laryngoscope blade that is capable of providing optimal clearance of the airway of a patient while not increasing time and/or costs to the user, and that maintains its effectiveness by remaining sleek and non-bulky in structure.

The preferred embodiment of the present invention is designed to solve the problems herein described and other problems not discussed, which are discoverable by a skilled artisan.

BRIEF DESCRIPTION OF THE DRAWINGS

These and other features and advantages of this invention will be more readily understood from the following detailed description of the various aspects of the invention taken in conjunction with the accompanying drawings in which:

FIG. 3 is a side view of a related art laryngoscope blade;

FIG. 4 is a side view of the laryngoscope blade of FIG. 1, as used in the airway of a patient;

FIG. 5 is a side view of the laryngoscope blade of FIG. 3, as used in the airway of a patient;

Figure 1:
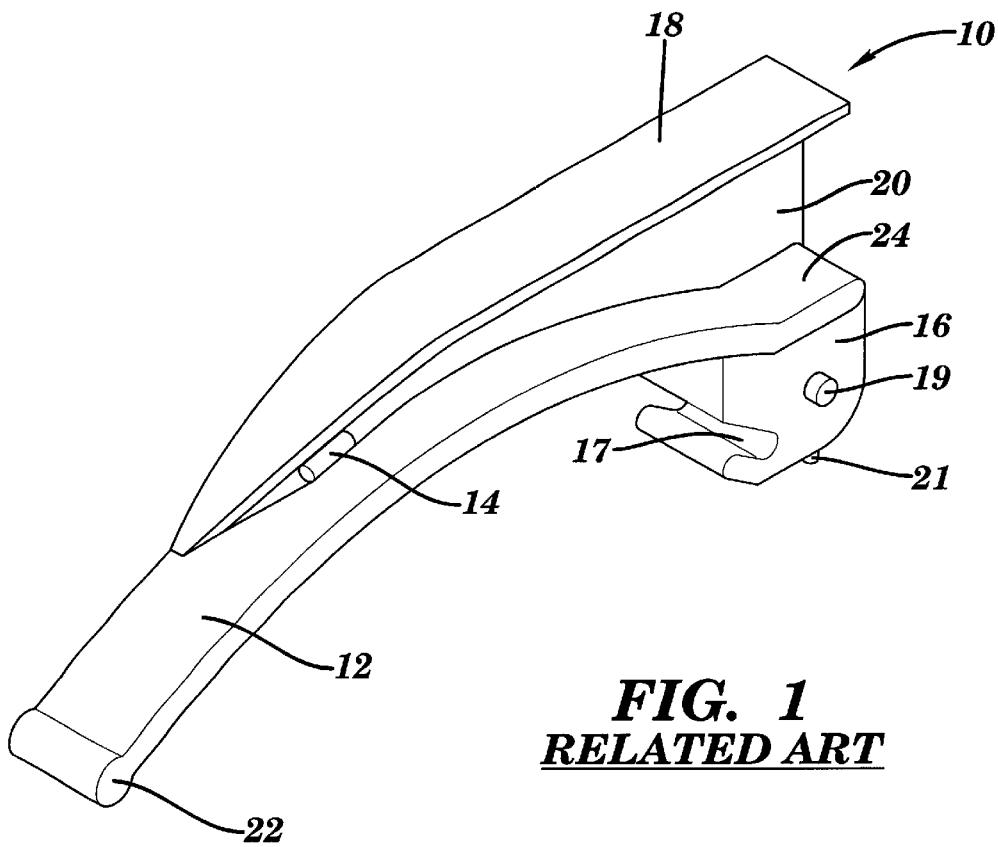
FIG. 1 is an isometric view of a related art laryngoscope blade.
Figure 2:
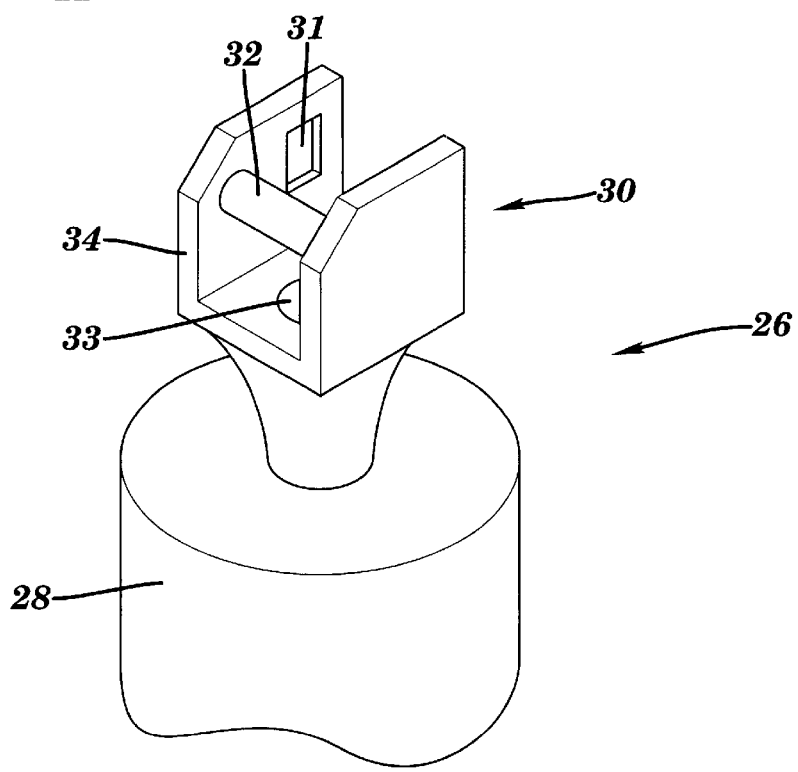
FIG. 2 is a partial isometric view of a related art handle for the laryngoscope blade of FIG. 1.

It is noted that the drawings of the invention are not to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements between the drawings.

DETAILED DESCRIPTION OF THE DRAWINGS

Referring first to FIGS. 1–5, related art devices are shown. In particular, FIG. 1 shows a related art laryngoscope blade 10 with a curved profile. The laryngoscope blade 10 is known to those of ordinary skill in the art as a "Macintosh" blade and generally includes a curved blade portion 12 having a proximal end 24, a distal end 22, sidewall 20, fin portion 18, base portion 16 and an optional light source 14. The laryngoscope blade 10 is designed to interconnect to a handle 26, such as that shown in FIG. 2. The handle 26 includes a cylinder 28 for storing a power source such as batteries or the like (not shown), and a support bracket 30 that is defined by a channel 34, a beam 32, a notch 31, and an electrical contact 33.

To achieve attachment of the laryngoscope blade 10 to the handle 26, the base portion 16 of the laryngoscope blade 10 will connect to support bracket 30 of the handle 26. This is accomplished by fitting a groove 17 of the base portion 16 around the beam 32 and locking a protrusion 19 of the base portion 16 into the notch 31 of the support bracket 30. Once the connection has been made, an electrical lead 21 of the base portion 16 will make contact with the electrical contact 33 of the support bracket 30. The power source stored in the cylinder of the handle will then illuminate the light source 14 disposed adjacent the blade portion 12. The transmission of power from the power source to the light source 14 is well known to those of ordinary skill in the art and can be accomplished by any number of known methods, such as that disclosed in U.S. Pat. No. 5,702,351 to Bar-Or et al.

Referring now to FIG. 3, another related art laryngoscope blade 36 is shown. Specifically, the laryngoscope blade 36 shown is known as a "Miller" blade and maintains a substantially straight profile. Similar to the Macintosh laryngoscope blade 10 of FIG. 1, the Miller laryngoscope blade 36 of FIG. 3 includes a blade portion 40 having a proximal end 44, a distal end 46, a side wall 48, a light source 38 and a base portion 42. The base portion 42 is identical to that shown on the Macintosh laryngoscope blade 10 so that it can be attached to the handle 26 in the same manner. In particular, the base portion 42 of the Miller laryngoscope blade 36 includes a groove 46, a protrusion 50, and an electrical lead 48 that interconnects with the electrical contact 33 of the handle 26 in the same manner as described above.

Once the laryngoscope device has been assembled, it can then be inserted into the airway of a patient 55 to achieve intubation. Referring now to FIGS. 4 and 5, assembled laryngoscope devices 52, 53 are shown. Specifically, FIG. 4 depicts a laryngoscope device 52 with a Macintosh laryngoscope blade 10 and FIG. 5 depicts a laryngoscope device 53 with a Miller laryngoscope blade 36. Referring first to FIG. 4, the laryngoscope device 52 is inserted into a patient's airway 54. Once inserted, the distal end 22 of the Macintosh laryngoscope blade 10 is inserted into the vallecula 60, which is the crevice/depression directly anterior the peak-like epiglottis 58. This insertion results in an opening of the patient's glottic opening 57 so that the vocal cords 56 are exposed and a medical tube or the like can be inserted through the patient's airway.

The Miller laryngoscope blade 36 of FIG. 5 is utilized in a slightly different manner. Specifically, the distal end 46 of the Miller laryngoscope blade 36 extends beyond the vallecula 60 and anteriorly displaces the patient's epiglottis 58 manually. Similar to the Macintosh laryngoscope blade 10, the Miller laryngoscope blade 36 will open the glottic opening 57 for intubation of the patient 55. It should be understood that the type of laryngoscope blade used will vary based on a plurality of factors such as size of the patient 55 or the preference of the medical professional performing the procedure. In addition, it should be appreciated that laryngoscope blades are available in many distinct sizes and shapes and the related art devices described herein are only for background purposes.

Figure 6:
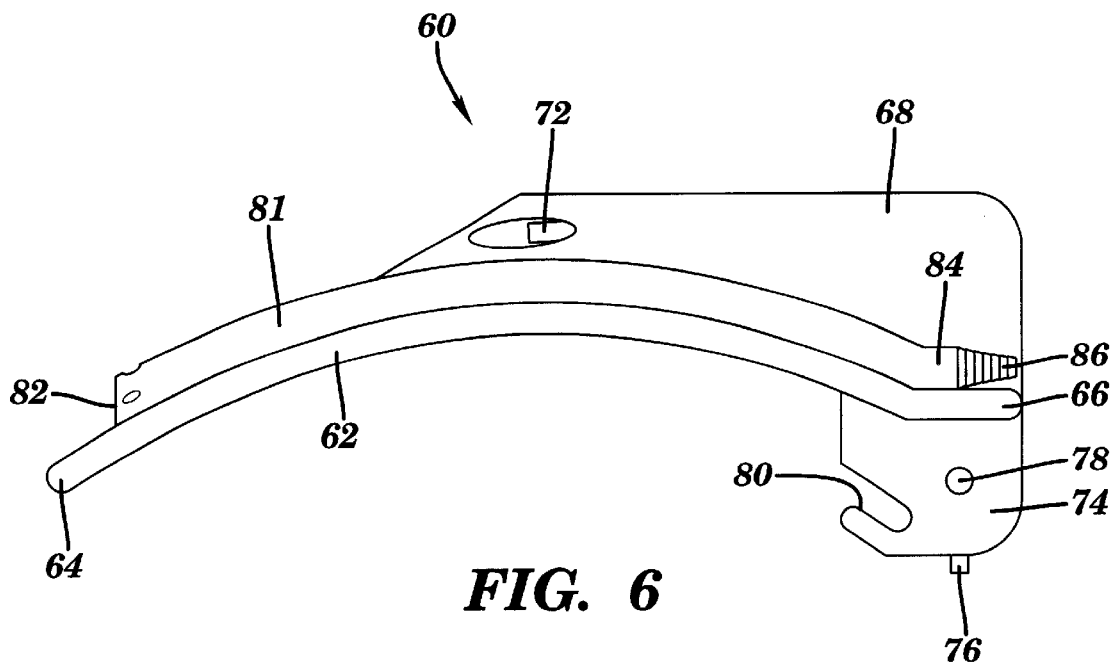
FIG. 6 is a side view of a laryngoscope blade, in accordance with the present invention.
Figure 7:
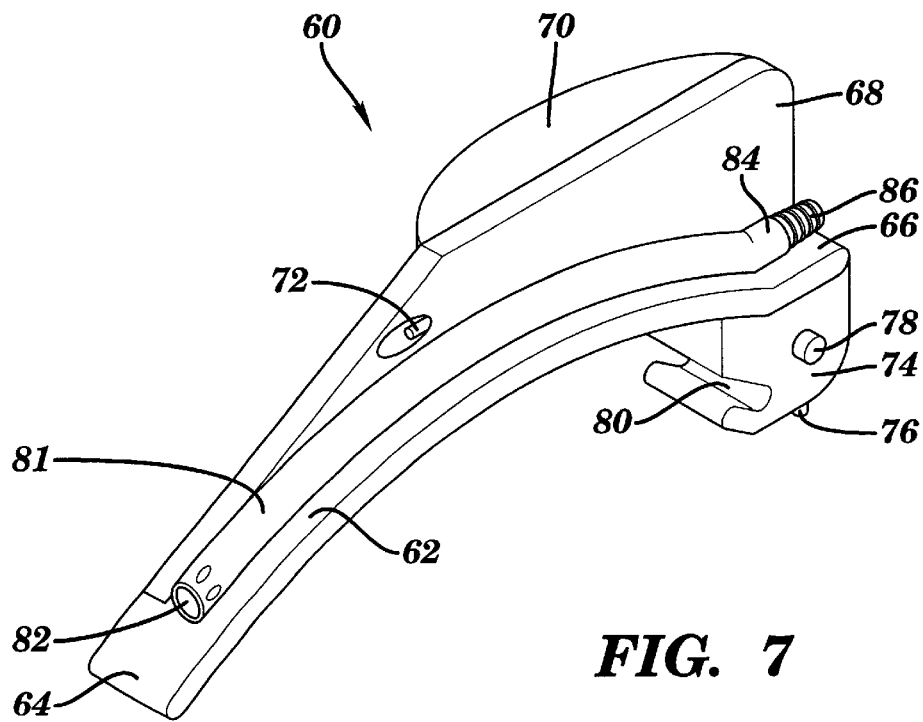
FIG. 7 is an isometric view of the laryngoscope blade of FIG. 6.

FIGS. 6–9 depict the laryngoscope blades of the present invention. Referring first to FIGS. 6 and 7, an improved laryngoscope blade 60 is depicted. In particular, laryngoscope blade 60 includes a curved blade portion 62, having a first or proximal end 66 and a second or distal end 64.

Attached to the blade portion 62 is a side wall 68 on which is positioned an optional light source 72. Attached to sidewall 68 is a fin 70. Attached to the blade portion 62, at a position adjacent the proximal end 66 is a base portion 74. It should be appreciated that the precise configuration and arrangement of these components is not essential. In particular, it should be appreciated that the light source 72 can be disposed at various positions along the laryngoscope blade 60. In addition, it should be understood that the blade portion 62 need not be curved.

Similar to the base portion 16 of the related art Macintosh blade 10 shown in FIG. 1, the base portion 74 of the present laryngoscope blade 60 includes a protrusion 78, an electrical lead 76, and a groove 80. The design of base portion 74 is such that the laryngoscope blade 60 of the present invention can interconnect with the handle 26 of FIG. 2 in the same manner as related art devices. Specifically, groove 80 will engage the beam 32 of the support bracket 30 of the handle 26. As this occurs, the protrusion 78 will engage the notch 31 as the electrical lead 76 connects with the electrical contact 33, thus connecting the power source (not shown) with the light source 72. This compatibility of the present laryngoscope blade 60 with existing handles 26 will prevent additional costs to the consumer. With many related art laryngoscope blades, a user is required to purchase a new handle that is unique to the particular laryngoscope blade.

A feature incorporated into the laryngoscope blade 60 of the present invention is the suction tube 81. In particular, the present invention includes a suction tube 81 permanently fixed/coupled to an exterior surface of the blade portion 62, on a side opposite the base portion 74. This is such that the suction tube 81 is a permanent component of the laryngoscope blade 60. With such a design, the profile of the laryngoscope blade 60 remains sleek or minimal. In related art laryngoscope blades, tubing must be inserted by a user if suction is desired. Such embodiments lead to additional costs in the purchase and/or sanitization of the blade 60 as well as reduced suctioning of the patient's airway if the suction tubing is not sufficiently secured to the blade. In addition, many related art devices that attempt to incorporate suction capability into the laryngoscope blade add bulk to the instrument. As shown in FIGS. 4, 5, 10, and 11, the patient's airway 54 is extremely narrow and bulkier laryngoscope devices may not only obstruct the airway of a patient 55 but are also more difficult to insert into the proper positions.

Figure 10:
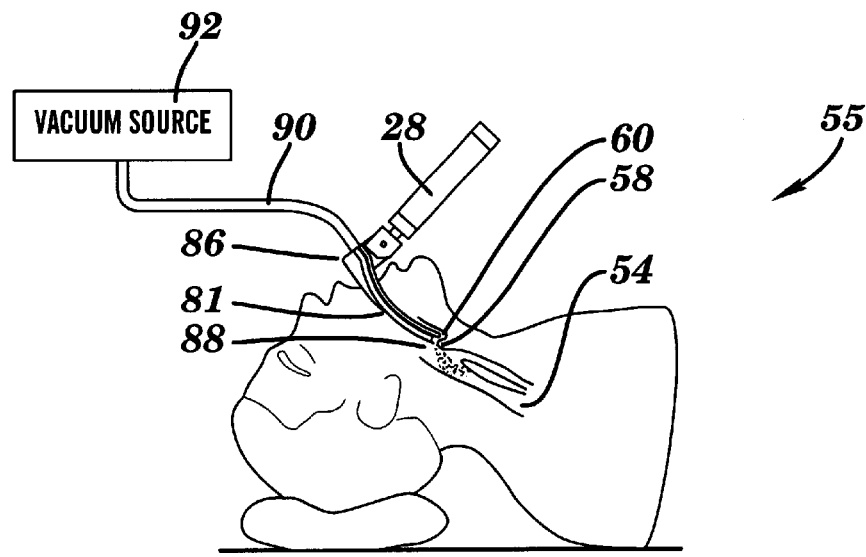
FIG. 10 is a side view of the laryngoscope blade of FIG. 6, as used in the airway of a patient.

The suction tube 81 is preferably welded to the blade portion 62 or machined as a component of the blade 60 during original construction of the blade 60. In addition, the suction tube 81 generally includes a suction end 82 and an adaption end 84. As shown in FIGS. 6 and 7, an adapter 86 is disposed at adaption end 84. The adapter 86 is to provide connection of the suction tube 81 to a suction source 92, as shown in FIG. 10. Preferably, adapter 86 is positioned in adaption end 84 and connects to a suction catheter 90, which connects to a suction/vacuum source 92. Although adapter 86 can take varying shapes and dimensions, a ridged, stepped adapter 86 is preferred. In addition, adapter 86 is preferably formed as a permanent component of the suction tube. However, it should be realized that suction tube 81 can be made without the adapter 86, in which case a user would insert the adapter 86 into the suction tube 81 manually.

Once connected to the suction/vacuum source 92, any debris 88, such as blood, vomit, or the like, can be removed from the patient's airway 54. Preferably, the suction end 82 of the suction tube 81 is positioned approximately 2 centimeters from the distal end 64 of the blade portion 62. This enables the suction tube 81 to have a sleek profile and minimal structure, which prevents the laryngoscope blade 60 from improperly obstructing the patient's airway. It should be appreciated, however, that the precise positioning of the suction tube 81 may vary and that 2 centimeters is the preferred positioning.

Referring now to FIG. 10, the laryngoscope blade 60 is depicted in use. Similar to the related art device of FIG. 4, the laryngoscope blade 60 will enter the airway of a patient 55. The distal end 64 will then be inserted into the patient's vallecula 60, which is directly behind the patent's epiglottis 58. Once inserted, any debris 88 in the patient's airway can be suctioned out. As described above, this is accomplished by attaching the suction catheter 90 the adapter 86 and into the suction/vacuum source 92 to provide suction through the suction tube 81.

Figure 8:
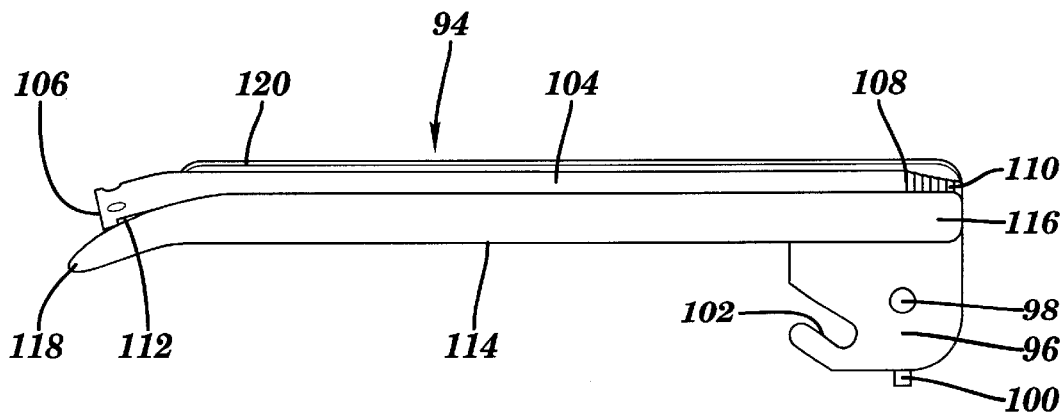
FIG. 8 is a side view of a laryngoscope blade, in accordance with the present invention.
Figure 9:
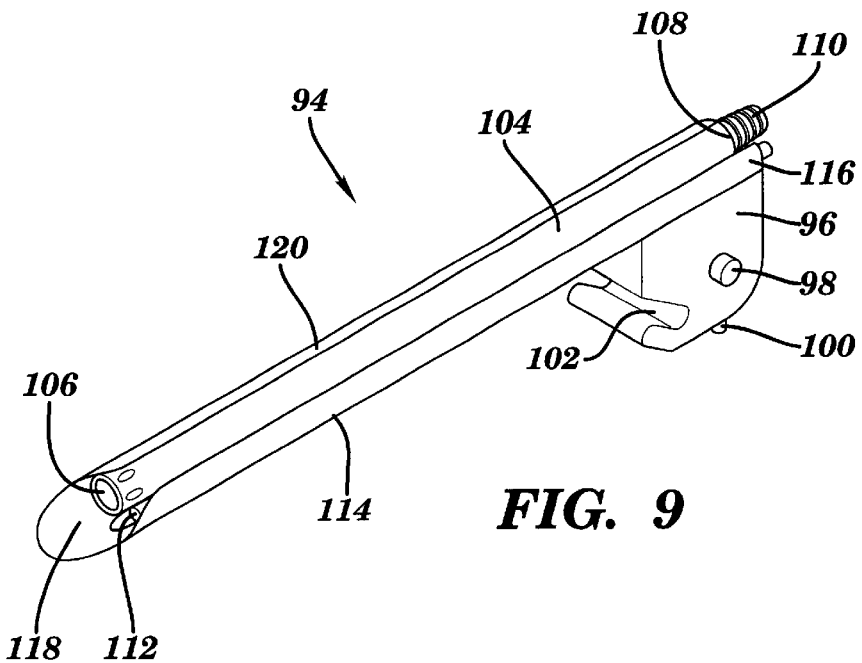
FIG. 9 is an isometric view of the laryngoscope blade of FIG. 8.

Referring now to FIGS. 8 and 9, an additional an improved laryngoscope blade 94 is depicted. In particular, laryngoscope blade 94 includes a substantially straight blade portion 114 having a first or proximal end 116 and a second or distal end 118. Attached to the blade portion 114 is curved side wall 120. Optionally, a light source 112, may be positioned adjacent the blade portion 114, proximate the distal end 118. Attached to blade portion 114, at a position near the proximal end 116 is a base portion 96. It should be appreciated that the precise configuration and arrangement of these components is not essential. In particular, it should be appreciated that the light source 112 need not necessarily be disposed at the position indicated, rather, its position may vary. In addition, it should be understood that the precise configuration of the blade portion 114 need not be entirely straight. For instance, the distal end 118 may be curved, as shown in FIG. 8, or it may be straight so as to be in alignment with the blade portion 114.

Similar to the base portion 42 of the related art Miller blade 36 shown in FIG. 3, the base portion 96 of the present laryngoscope blade 94 includes a protrusion 98, an electrical a lead 100, and a groove 102. The design of base portion 96 is such that the laryngoscope blade 94 of the present invention can interconnect with the handle 26 of FIG. 2 in the same manner as related art devices. Specifically, groove 102 will engage the beam 32 of the support bracket 30 of the handle 26. As this occurs, protrusion 98 will engage notch 31 as the electrical lead 100 connects with the electrical contact 33, thus connecting the power source (not shown) with the light source 112. This compatibility of the present laryngoscope blade 94 with existing handles 26 will prevent additional costs to the consumer. Specifically, with many related art laryngoscope blades, a user is required to purchase a new handle that is unique to the particular laryngoscope blade.

Similar to the laryngoscope blade 60 described above, a feature incorporated into the laryngoscope blade 94 of the present invention is a suction tube 104. In particular, the laryngoscope blade 94 includes a suction tube 104 permanently fixed/coupled to an exterior surface of the blade portion 114, on a side opposite the base portion 96. This is such that the suction tube 104 is a permanent component of the laryngoscope blade 94. With such a design, the bulk/structure of the laryngoscope blade 94 remains sleek or minimal. In related laryngoscope blades, tubing must be inserted by a user if suction is desired. Such embodiments lead to additional costs in the purchase and/or sanitization of the blade 94 as well as reduced suctioning of the patient's airway 54 if the suction tubing is not sufficiently secured to the blade. In addition, many related art devices that attempt to incorporate suction capability into the laryngoscope blade add bulk to the instrument. As shown in FIGS. 4, 5, 10, and 11, the patient's airway 54 is extremely narrow, and bulkier laryngoscope devices may not only obstruct the airway of a patient 55 but are also more difficult to insert into the proper positions.

Figure 11:
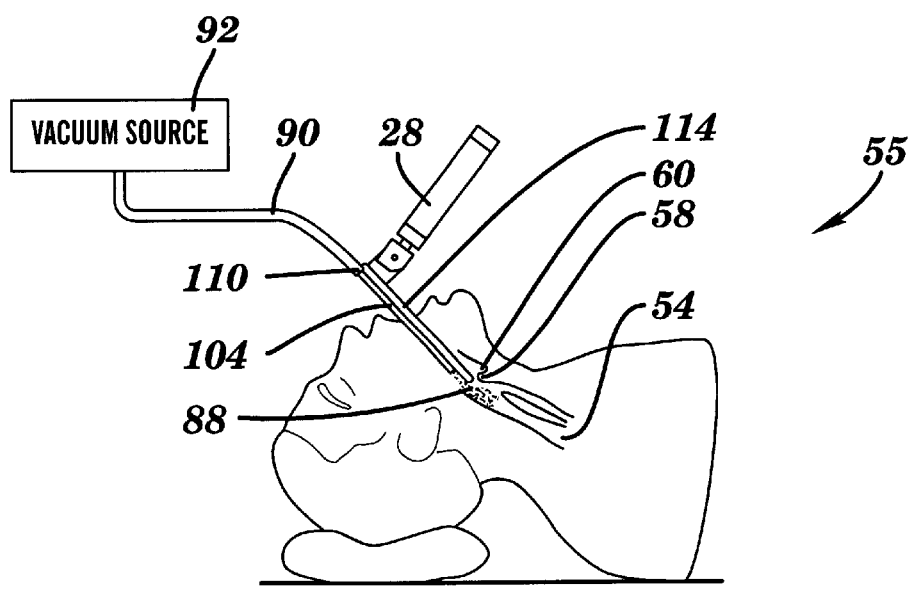
FIG. 11 is a side view of the laryngoscope blade of FIG. 7, as used in the airway of a patient.

The suction tube 104 is preferably welded to the blade portion 114 or is machined as a component of the blade 94 during the original construction of the blade 94. In addition, the suction tube 104 generally includes a suction end 106 and an adaption end 108. As shown in FIGS. 8 and 9, an adapter 110 is disposed at adaption end 108. The adapter 110 is to provide connection of the suction tube 104 to a suction/vacuum source 92, as shown in FIG. 11. Preferably, adapter 110 is positioned in adaption end 108 and connects to a suction catheter 90, which connects to a suction/vacuum source 92. Although the adapter 110 can take varying shapes and dimensions, a ridged, stepped adapter 110 is preferred. In addition, adapter 110 is preferably formed as a permanent component of the suction tube 104. However, it should be understood the suction tube 104 could be made without the adapter 110, in which case a user would insert the adapter 110 into the suction tube 104 manually.

Once connected to a suction/vacuum source 92, any debris, such as blood, vomit, or the like, can be removed from the patient's airway 54. In addition, the suction end 106 of the suction tube 104 is preferably positioned approximately 1–1.5 centimeters back from the distal end 118 of the blade portion 114. This enables the suction tube 104 to have a sleek profile and minimal structure, which prevents the laryngoscope blade 94 from improperly obstructing the patient's airway. It should be appreciated, however, that the precise positioning of the suction tube 104 may vary and that 1 centimeter is the preferred positioning.

Referring to FIG. 11, the laryngoscope blade 94 is depicted in use. Similar to the related art device of FIG. 5, the laryngoscope blade 94 will enter the airway 54 of a patient 55. The distal end 118 will then anteriorly displace the patient's epiglottis 58. Once inserted, any debris 88 in the patient's airway can be suctioned out. As described above, this is accomplished by inserting an adapter 110 into the adaption end 108 of the suction tube 104. Then, the suction catheter 90 is attached to the adapter 110 and into the suction/vacuum source 92 to provide suction through the suction tube 104.

It should be understood that the laryngoscope blades of the present invention are preferably stainless steel. However, it should be appreciated that the precise metal used may vary. Stainless steel is advantageous due to its strength, resistance to corrosion, and ease of sterilization.

The foregoing description of the preferred embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

What is claimed is:

1. A laryngoscope blade, comprising:
   a blade portion; and
   a suction tube, wherein the suction tube is irremoveably integrated with an external surface of the blade portion.

2. The laryngoscope blade of claim 1, wherein the suction tube extends from a first point proximate a first end of the blade portion to a second point proximate a second end of the blade portion.

3. The laryngoscope blade of claim 1, wherein the suction tube has an adaption end and a suction end.

4. The laryngoscope blade of claim 3, wherein the adaption end includes an adapter.

5. The laryngoscope blade of claim 4, wherein the adapter is attachable to a suction catheter, and wherein the suction catheter is attachable to a suction source.

6. The laryngoscope blade of claim 1 further comprising a base portion, positioned proximate a first end of the blade portion, wherein the base portion is attachable to a handle.

7. The laryngoscope blade of claim 1, further comprising a light source disposed proximate the blade portion.

8. The laryngoscope blade of claim 1, wherein the blade portion is curved.

9. The laryngoscope blade of claim 1, wherein the blade portion is substantially straight.

10. The laryngoscope blade of claim 1, wherein the blade portion and the suction tube are metal.

11. The laryngoscope blade of claim 1, wherein the suction tube is formed as a permanent component of the blade portion during construction of the blade portion.

12. The laryngoscope blade of claim 1, wherein the suction tube is welded to the external surface of the blade portion.

13. A laryngoscope blade, comprising:
    a metal blade portion; and
    a metal suction tube irremoveably fixed to an external surface of the blade portion adjacent a side wall.

14. The laryngoscope blade of claim 13, further comprising a base portion positioned proximate the blade portion.

15. The laryngoscope blade of claim 13, further comprising a handle, wherein the laryngoscope blade couples to the handle.

16. The laryngoscope blade of claim 15, wherein the handle includes a power source for illuminating a light source disposed on the blade portion.

17. The laryngoscope blade of claim 13, wherein the suction tube has an adaption end and a suction end.

18. The laryngoscope blade of claim 17, wherein the adaption end includes an adapter at a location proximate the base portion.

19. The laryngoscope blade of claim 17, wherein the adaption end is attachable to a suction catheter, and wherein the suction catheter is attachable to a suction source.

20. A laryngoscope blade, comprising:
    a blade portion having an external surface and a side wall;
    a suction tube irremoveably integrated with the external surface of the blade portion adjacent the sidewall, wherein the suction tube includes an adaption end and a suction end; and
    wherein the adaption end is attachable to a suction source.

* * * * *